United States Patent
Liu et al.

(10) Patent No.: US 8,598,399 B2
(45) Date of Patent: Dec. 3, 2013

(54) CATALYST COMPOSITION FOR DIRECT CONVERSION OF ETHANOL TO PROPYLENE

(75) Inventors: Yu Liu, Lake Jackson, TX (US); Andrzej M. Malek, Midland, MI (US); Albert E. Schweizer, Jr., Port St. Lucie, FL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/576,431

(22) PCT Filed: Mar. 7, 2011

(86) PCT No.: PCT/US2011/027378
§ 371 (c)(1), (2), (4) Date: Sep. 4, 2012

(87) PCT Pub. No.: WO2011/112503
PCT Pub. Date: Sep. 15, 2011

(65) Prior Publication Data
US 2012/0330080 A1    Dec. 27, 2012

Related U.S. Application Data

(60) Provisional application No. 61/311,551, filed on Mar. 8, 2010.

(51) Int. Cl.
*C07C 1/00* (2006.01)

(52) U.S. Cl.
USPC ............. 585/640; 585/638; 585/639; 502/71; 502/77; 502/241

(58) Field of Classification Search
USPC ................................................ 585/638–640
See application file for complete search history.

(56) References Cited

U.S. PATENT DOCUMENTS

| | | | |
|---|---|---|---|
| 5,783,321 A | 7/1998 | Verduijn et al. | |
| 5,990,365 A * | 11/1999 | Chang et al. | 585/475 |
| 6,013,239 A | 1/2000 | Chen et al. | |
| 6,180,550 B1 | 1/2001 | Beck et al. | |
| 6,184,167 B1 | 2/2001 | Van Mao et al. | |
| 6,239,057 B1 | 5/2001 | Ichikawa et al. | |
| 6,261,534 B1 | 7/2001 | Miller | |
| 6,277,355 B1 | 8/2001 | Kennedy et al. | |
| 6,368,571 B1 | 4/2002 | Vempati | |
| 6,504,075 B2 | 1/2003 | Beck et al. | |
| 6,800,272 B2 | 10/2004 | Kulkarni et al. | |
| 6,908,303 B1 | 6/2005 | Oda et al. | |
| 7,344,695 B2 | 3/2008 | Xu et al. | |
| 7,361,328 B2 | 4/2008 | Kim et al. | |
| 7,585,804 B2 | 9/2009 | Smith et al. | |
| 7,601,330 B2 | 10/2009 | Wang et al. | |
| 2006/0025646 A1 | 2/2006 | Fung et al. | |

FOREIGN PATENT DOCUMENTS

WO    2007114195 A1    10/2007

OTHER PUBLICATIONS

Barthos et al. Decomposition and Aromatization of Ethanol on ZSM-Based Catalysts. J. Phys. Chem. B. 2006, 110 pp. pp. 21816-21825.*
Hamdam et al. Structural Characterization of Rhenium Impregnated Zeolite Y and ZSM-5 by 29Si and 27AI MAS NMR Spectroscopy. Studies in Surface Science and Catalysis. vol. 83, 1994, pp. 125-132 http://www.sciencedirect.com/science/article/pii/S0167299108632504.*
PCT/US2011/027378, International Search Report and Written Opinion.
PCT/US2011/027378, International Preliminary Report on Patentability.
Barthos, J. Phys. Chem. B, 2006, 110, 21816-21825.
Hamdan, Studies in Surface Science and Catalysis, 1994, 83, 125-132.
Iwamoto, Abstracts of Papers, 235th ACS National Meeting, 2008 "Highly selective formation of lower olefins from bioethanol on nickel ion-loaded mesoporous silica catalysts."
Iwamoto, J. Phys. Chem C, 2007, 111, 12.
Oikawa, Appl. Catal. 2006, 312, 181.
Song, Catalysis Letters, 2009, Production of propylene from ethanol over ZSM-5 zeolites.
Wang, Journal of Catalysis, 2000, 190, 276-283.
PCT/US2011/027378, International Search Report and Written Opinion, Apr. 2011.
PCT/US2011/027378, International Preliminary Report on Patentability, Apr. 2011.

* cited by examiner

*Primary Examiner* — Walter D Griffin
*Assistant Examiner* — Jelitza Perez

(57) ABSTRACT

A process to prepare propylene showing desirably increased selectivity comprises contacting, at an elevated temperature, ethanol and a rhenium oxide-modified ZSM-5 zeolite catalyst, under conditions suitable to form propylene. The rhenium oxide-modified ZSM-5 zeolite catalyst may be prepared by impregnating, in an aqueous or organic medium, a ZSM-5 zeolite with a rhenium source, under conditions suitable to form a catalyst precursor, and calcining the catalyst precursor under conditions suitable to form a rhenium oxide-modified ZSM-5 zeolite catalyst.

9 Claims, No Drawings

CATALYST COMPOSITION FOR DIRECT CONVERSION OF ETHANOL TO PROPYLENE

This application is a non-provisional application claiming priority from the U.S. Provisional Patent Application No. 61/311,551, filed on Mar. 8, 2010, entitled "CATALYST COMPOSITION FOR DIRECT CONVERSION OF ETHANOL TO PROPYLENE" the teachings of which are incorporated by reference herein, as if reproduced in full hereinbelow.

BACKGROUND

1. Field of the Invention

The invention relates to the conversion of ethanol to propylene. More particularly, it relates to the direct conversion of ethanol to propylene using a modified ZSM-5 zeolite catalyst.

2. Background of the Art

Propylene is an important starting material for a wide range of materials used in producing both durable and nondurable goods. While its price is currently subject to significant fluctuation, there remains an industrially important supply and demand market at a level of millions of metric tons (billions of pounds) per year.

Propylene is most typically produced as a by-product of either ethylene production or refinery operations. Where it is produced in connection with ethylene production, a steam cracking process uses heat to produce a mixture of hydrocarbons, and specific products, such as propylene, may then be isolated by distillation. Significant quantities of propylene are produced when naphtha is used as the steam cracking feedstock. Where it is produced as a by-product of refinery operations, catalytic cracking of heavier petroleum fractions may be carried out. Unfortunately, the fact that both of these routes begin with petroleum, which is subject to supply and price fluctuations, the cost of producing propylene, and therefore the demand for it, likewise varies. This makes it difficult for producers to maintain acceptable margins and anticipate future demands. Because of these issues, alternative starting materials for propylene production have been sought.

In recent years much research has gone into methods to produce desirable hydrocarbon products from renewable sources, such as biomass that results from fermentation. Such sources include various plants, including, for example, sugar cane. Production of ethanol from such sources has been highly successful. Because of this success, the possibility of producing propylene from bio-resourced ethanol has arisen. However, most known methods suffer from relatively low propylene yield. Identification of ways to increase propylene yields from ethanol are therefore now highly desired.

SUMMARY OF THE INVENTION

In one embodiment, the present invention provides a process to prepare propylene comprising contacting, at an elevated temperature, ethanol and a rhenium oxide-modified ZSM-5 zeolite catalyst, under conditions suitable to form propylene. The process may comprise first preparing the rhenium oxide-modified ZSM-5 zeolite catalyst composition by impregnating, in an aqueous or organic medium, a ZSM-5 zeolite with a rhenium source, under conditions suitable to form a catalyst precursor, and calcining the catalyst precursor under conditions suitable to form a rhenium oxide-modified ZSM-5 zeolite catalyst composition.

DETAILED DESCRIPTION OF THE EMBODIMENTS

The invention provides a process that produces higher yield in the conversion of ethanol to propylene than many other known catalysts, including other zeolites such as unmodified ZSM-5. The inventive process includes using a rhenium oxide-modified ZSM-5 zeolite catalyst. For convenience herein, the oxide of rhenium present on or in the ZSM-5 zeolite is referred to by the generalized symbol "ReOx," regardless of the original source of the rhenium or of the oxygen. Thus, the rhenium oxide-modified ZSM-5 zeolite catalyst is referred to generally as "ReOx/ZSM-5."

The ReOx/ZSM-5 may be prepared beginning with any known method of preparing a non-modified ZSM-5 zeolite, or an unmodified ZSM-5 zeolite may be obtained commercially. Those skilled in the zeolite art will be well-aware that the X-ray diffraction pattern by which this family of crystalline compositions is characterized is that comprised in Table 1 hereinbelow.

TABLE 1

| Interplanar Spacing d (Å)[1] | Range | Relative intensity, I/I$_o$ |
|---|---|---|
| 11.1 | +/−0.3 | S |
| 10.0 | +/−0.3 | S |
| 7.4 | +/−0.2 | W |
| 7.1 | +/−0.2 | W |
| 6.3 | +/−0.2 | W |
| 6.04 | +/−0.2 | W |
| 5.56 | +/−0.1 | W |
| 5.01 | +/−0.1 | W |
| 4.60 | +/−0.08 | W |
| 4.25 | +/−0.08 | W |
| 3.85 | +/−0.07 | Vs |
| 3.71 | +/−0.05 | S |
| 3.04 | +/−0.03 | W |
| 2.99 | +/−0.02 | W |
| 2.94 | +/−0.02 | W |

[1]Å is Angstroms. 10 Angstroms equals 1 nanometer (nm).

The values in Table 1 are determined by standard techniques, well known to those skilled in the art of crystallography, and are based on use of radiation, that is the K-alpha doublet of copper, and a scintillation counter spectrometer with a strip chart pen recorder. The peak heights, I, and their positions as a function of 2 times theta (ω), where theta is the Bragg angle, are read from the spectrometer chart. From these, the relative intensities 100 I/I$_o$, where I$_o$ is the intensity of the strongest peak, and d (observed), which is the interplanar spacing in angstroms (Å), corresponding to the recorded peaks, may be calculated. The relative intensities are given in Table 1 in terms of the symbols w=weak, s=strong, and vs=very strong. It should be understood that this X-ray diffraction pattern is characteristic of all the species of ZSM-5 zeolites. Ion exchange of one cation for another reveals substantially the same pattern, with some minor shifts in interplanar spacings and variations in relative intensities. Other minor variations can occur depending upon the ratio of the oxides' cations in the particular sample, as well as whether or not the composition has been subjected to thermal treatment.

Furthermore, the compositions are also identified, in terms of mole ratios of oxides, as follows:

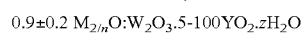

$$0.9 \pm 0.2\ M_{2/n}O:W_2O_3.5\text{-}100YO_2.zH_2O$$

wherein M is a cation, for example, ammonium ($NH_4^+$), sodium ($Na^+$) or calcium ($Ca^{2+}$), n is the valence of that cation, W is selected form the group consisting of aluminum and gallium, Y is selected from the group consisting of silicon and germanium, and z is from 0 to 40. In a preferred synthesized form, this zeolite has a formula, in terms of mole ratios of oxides, as follows:

$$0.9 \pm 0.2\ M_{2/n}O:Al_2O_3 \cdot 5\text{-}100 SiO_2 \cdot zH_2O$$

More preferably, the mole ratio of $SiO_2$ to $Al_2O_3$ ranges from 30 to 80, and still more preferably from 40 to 60.

Preparation of these catalysts may be accomplished by preparing solutions containing tetrapropyl ammonium hydroxide, sodium oxide, an oxide of aluminum or gallium, an oxide of silica or germanium, and water, and mixing these solutions to obtain a gel having a composition, in terms of mole ratios of oxides, falling within the ranges shown in Table 2.

TABLE 2

| Oxides | Broad range | Preferred range | Particularly preferred range |
|---|---|---|---|
| OH$^-$/YO$_2$ | 0.07-10.0 | 0.1-0.8 | 0.2-0.75 |
| R$_4$N$^+$/(R$_4$N$^+$ + Na$^+$) | 0.2-0.95 | 0.3-0.9 | 0.4-0.9 |
| H$_2$O/OH$^-$ | 10-300 | 10-300 | 10-300 |
| YO$_2$/W$_2$O$_3$ | 5-100 | 30-80 | 40-60 | wherein R is propyl, W is aluminum or gallium, and Y is silicon or germanium, maintaining the mixture until crystals of the zeolite are formed. It is noted that an excess of tetrapropyl-ammonium hydroxide can be used, which would raise the value of OH$^-$/YO$_2$ above the ranges set forth supra. In that case, the excess hydroxide would not participate in the reaction. Thereafter, the crystals may be separated from the liquid and recovered. Typical reaction conditions consist of heating the foregoing reaction mixture to a temperature from about 100 degrees Celsius (° C.) to 175° C. for a period of time from about 6 hours to 60 days. A more preferred temperature range is from about 150° C. to 175° C., with the amount of time at a temperature in this range being from about 12 hours to 8 days.

The digestion of the gel particles is typically carried out until crystals form. The solid product may be separated from the reaction medium, by means such as by cooling the whole to room temperature, filtering and water washing.

The product may then be dried for a time period and at a temperature sufficient to remove substantially all of the residual water from the crystallization process. For example, in some embodiments this may be conveniently accomplished by drying at a temperature of 110° C. for a period from 8 to 24 hours. Milder conditions may be employed if desired, for example, room temperature and/or under vacuum.

ZSM-5 is preferably formed as an aluminosilicate. The appropriate oxides used in the preparation of ZSM-5 may include, for example, sodium aluminate, alumina, sodium silicate, silica hydrosol, silica gel, silicic acid, sodium hydroxide, tetrapropylammonium compounds, such as tetrapropylammonium hydroxide, or combinations thereof. It will be understood that each oxide component utilized in the reaction mixture for preparing a member of the ZSM-5 family can be supplied by one or more initial reactants and they can be mixed together in any order. For example, sodium oxide can be supplied by an aqueous solution of sodium hydroxide, or by an aqueous solution of sodium silicate, and tetrapropylammonium cation can be supplied by the bromide salt. The reaction mixture can be prepared either batchwise or continuously. Crystal size and crystallization time of the ZSM-5 zeolite will vary with the nature of the reaction mixture employed.

Once the unmodified ZSM-5 has been prepared, whether as a crystalline powder or, in combination with a binder, as an engineered extrudate, or has been obtained commercially in either form from a supplier, it is modified by impregnation with a selected source, or sources, of rhenium. Because rhenium can have any oxidation state between and including −1 to +7, with +7, +6, +4 and +2 being most common, there are a large number of rhenium compounds that may potentially serve as sources of the rhenium. The most common rhenium compounds are the oxides and halides exhibiting a broad oxidation number spectrum, including $Re_2O_7$, $ReO_3$, $Re_2O_5$, $ReO_2$, and $Re_2O_3$, $ReF_7$, $ReCl_6$, $ReCl_5$, $ReCl_4$ and $ReCl_3$. Also included as rhenium sources are sulfides such as $ReS_2$ and $Re_2S_7$. $Re^{+7}$ oxide (also called dirhenium heptoxide ($Re_2O_7$)) is mildly acidic and can form a salt, such as, for example, $NH_4ReO_4$. For purposes of the invention, and for reasons of availability and cost, $NH_4ReO_4$ may, in certain embodiments, be preferred. While rhenium salts with cations other than $NH_4^+$ are known, for example, with $Na^+$ or $K^+$ cations as $NaReO_4$ and $KReO4$, the ammonium salt is preferred because it decomposes to rhenium oxide and volatile nitrogen compounds, and does not contaminate the catalyst with other metal residue during calcination. Combinations of any of the above rhenium sources may also be employed.

It should be noted that, because the goal is modification of the ZSM-5 zeolite with a rhenium oxide, a source of oxygen (beyond that already inherently present in the ZSM-5 zeolite's lattice structure) is also necessary to the inventive process. However, it is not necessary that the source of additional oxygen be present in the catalyst precursor. As defined herein, the catalyst precursor includes at least rhenium in combination with the ZSM-5 zeolite. Thus, the source of oxygen that is necessary to effect the formation of rhenium oxide during calcination may, in fact, be oxygen that is initially present in the rhenium source (for example, $NH_4ReO_4$), but in other embodiments the oxygen source may instead be the medium used for combining the rhenium source and the ZSM-5 zeolite, i.e., water and/or an organic such as an alcohol, an ether, or a combination thereof; or in yet other embodiments it may be oxygen or oxygen-containing gas that can be added during calcination of the catalyst precursor.

Preparation of the ReOx/ZSM-5 may be carried out by any suitable method, such as an incipient wetness impregnation method. The incipient wetness impregnation method may be accomplished by first dissolving the rhenium source(s) and the unmodified ZSM-5 zeolite together in an aqueous or organic solution. Then, in this embodiment, the solution may be added to a catalyst support, for example, to an alumina support, containing the same pore volume as the volume of solution that is being added. Capillary action draws the solution into the pores. The catalyst may then be dried and calcined to drive off the volatile components within the solution, depositing the rhenium source(s) on the catalyst surface and forming the catalyst precursor. The maximum loading is limited by the solubility of the rhenium source(s) in the solution, while the concentration profile of the impregnation material depends on the mass transfer conditions within the pores during impregnation and drying. In preferred embodiments the amount of the rhenium source may range from 1 percent by weight (wt %) to 20 wt %, and preferably from 3 wt % to 16 wt %, based on the weight of the unmodified ZSM-5 zeolite. It is preferred that, in the final calcined ReOx/ZSM-5, the amount of rhenium oxide ranges from 0.5 wt %, more preferably from 3 wt %, and still more preferably from 6 wt %, based on the catalyst as a whole, to 15 wt %, and more preferably to 8 wt %. In one particularly preferred embodiment, the rhenium is present in an amount of 7 wt %.

For additional details concerning the wide variety of methods that have been developed by researchers to prepare both unmodified and modified ZSM-5 zeolites, the reader may wish to see also U.S. Pat. Nos. 3,702,886; 7,601,330; 7,585,804; 7,361,328; 7,344,695; 6,908,303; 6,800,272; 6,504,075; 6,368,571; 6,277,355; 6,261,534; 6,184,167; 6,180,550; 6,013,239; 5,990,365; and 5,783,321; and many others.

Regardless of preparation method, the dried product powder, which is ReOx/ZSM-5, is thereafter desirably calcined at a temperature ranging from 300° C. to 600° C., more desirably from 450° C. to 550° C., for a time of from 2 to 8 hours, desirably ranging from 3 hours to 5 hours. The purpose of the calcination is to activate the catalyst, which means that the rhenium and oxygen source(s), for example, the $NH_4ReO_4$, or another rhenium compound in the presence of vapor oxygen, an alcohol or an ether, are converted to form a rhenium oxide. Thus, nature of the conversion is any that chemical reaction that results in the rhenium oxide, including, for example, decomposition or oxidation.

The ReOx/ZSM-5 may be used in a variety of types of reactors for carrying out the conversion of ethanol to propylene. For example, a typical fixed-bed, continuous-flow reactor, for example, a carbon steel or a stainless steel reactor, may be used for large scale production purposes. The process of the invention may be carried out at any desired pressure, although atmospheric pressure may be preferred for reasons of convenience and expense. A thermocouple may be employed to determine the temperature in the center of the catalyst bed during the reaction. The catalyst is generally placed in the central zone of the reactor, following catalyst activation (i.e., calcination) as described hereinabove.

The ethanol feedstock may be pumped into a vaporizer and mixed with an inert diluent gas such as nitrogen, argon, steam or a mixture thereof. Flow rate will depend upon desirable output and reactor and bed dimensions. The ethanol feedstock, which may be, for example, a high purity product (greater than 90% purity, or in some cases greater than 99% purity) or an azeotropic mixture of ethanol and water, is then, in vaporized form, flowed across the catalyst bed where the conversion to propylene as well as other products is accomplished. Conditions generally include the requirement that the ethanol be at an elevated temperature, that is, a temperature higher than ambient temperature, when it comes into contact with the ReOx/ZSM-5 catalyst. Such temperature may conveniently range from, for example, 250° C. to 500° C., and in some embodiments may range from 300° C. to 400° C. Those skilled in the art will be easily able to determine suitable variations in effective reaction conditions. A gas chromatograph may be employed to identify most or all of the products.

While the ReOx/ZSM-5 is particularly useful for the conversion of ethanol to propylene, it may alternatively be used to accomplish other alcohol dehydration processes. Such may include, for example, conversion of propanol or butanol to form propylene, butylene, and/or pentylene, respectively.

Where propylene is the product being prepared, it may be used for a wide variety of purposes. These may include, in various embodiments, oxidation to form propylene glycol, which is used as a solvent, lubricant, and/or stabilizer in a variety of industrial and consumer products. These products may include, for example, pharmaceuticals, cosmetics, food, animal feed, plastics, resins, paints, coatings, detergents, de-icers, and heat-transfer fluids. The propylene may also be polymerized to form polypropylene, which is useful for indoor and outdoor carpeting, or oxidized to form propylene oxide, which is useful for making polyurethanes. Finally, propylene is used in the production of oxo chemicals, cumene, isopropyl alcohol, acrylic acid, and acrylonitrile, the last being a building block in making acrylonitrile butadiene styrene plastics. These plastics enjoy widespread uses in, for example, automotive parts, telephones and toys.

EXAMPLES

Examples 1-3 and Comparative Example A

Three different ReOx/ZSM-5 catalysts are synthesized using the incipient wetness method. To carry this out, amounts of $NH_4ReO_4$ are dissolved in deionized water and each is separately used to impregnate 5 milliliter (mL) samples of ZSM-5 zeolite ($SiO_2/Al_2O_3$ ratio=50), which have been pretreated at 500° C. for 2 hours in air. The impregnation is carried out by adding the $NH_4ReO_4$ solution dropwise to the ZSM-5, which is in vials in a solid oscillation vibration mixer. The amounts of $NH_4ReO_4$ are varied to provide for a rhenium content of, respectively, 3.5 wt % (Example 1), 7 wt % (Example 2), and 14 wt % (Example 3), based on the catalyst as a whole. The mixture is then dried at 100° C. overnight, and finally calcined at 500° C. for 4 hours to form the final catalysts.

Experiments are carried out to compare the activity and selectivity of the ReOx/ZSM-5 zeolite catalysts with an unmodified but otherwise identical ZSM-5 zeolite catalyst, in conversion of ethanol to propylene. A continuous flow micro reactor system is employed at ambient pressure. This reactor is a stainless steel tube having an internal diameter of ¼ inch and a length of 6 inches. Each catalyst is used in an amount of 200 milligrams (mg). For each trial the catalyst is positioned between quartz chips, ranging from 20 to 50 U.S. mesh size (840 to 297 microns (μ)) in the reactor. The reaction temperature is controlled at 300° C., 350° C., and 400° C., respectively, for product analysis purposes. Prior to the reaction, each catalyst is heated at 500° C. for 2 hours in argon to remove any moisture. Ethanol is fed into the reactor by means of a syringe pump having a flowrate of 0.003 gram per minute (g/min). Argon, flowing at a rate of 20 milliliters per minute (mL/min), is used as a diluent.

Product is analyzed using online gas chromatography and results are reported in Table 3. The results show in general that using the Re/ZSM-5 zeolite catalyst improves propylene yield at all three temperatures, when compared to ZSM-5 alone, and that the catalyst including specifically 7 wt % of rhenium offers the highest selectivity to propylene at all three product analysis temperatures.

TABLE 3

|  |  | Example | | | |
|---|---|---|---|---|---|
|  |  | Comparative Example (no | Example 1 3.5 wt % | Example 2 7 wt % | Example 3 14 wt % |
| 300° C. | Ethanol Selectivity to | 100 | 100 | 100 | 100 |
|  | Methane | 0.01 | 0.04 | 0.06 | 0.07 |
|  | Ethylene | 11.4 | 25.6 | 38.6 | 55.2 |
|  | Ethane | 0.4 | 0.7 | 0.9 | 0.8 |
|  | Propylene | 7.3 | 8.5 | 8.8 | 6.9 |
|  | Propane | 3 | 2 | 1.3 | 0.6 |
|  | Butene | 13.4 | 15.3 | 13.2 | 11.3 |
|  | Butane | 11.6 | 9.7 | 5.5 | 3.5 |
|  | C5 + C6 | 16.8 | 30.1 | 26.7 | 17.1 |
|  | Aromatics | 8.8 | 7.9 | 4.8 | 3.6 |
|  | $CO_x$ | 0.01 | 0.05 | 0.08 | 0.1 |
|  | $C2^=-C4^=$ | 32.1 | 49.4 | 60.6 | 73.4 |

TABLE 3-continued

| | | Example | | | |
|---|---|---|---|---|---|
| | | Comparative Example (no | Example 1 3.5 wt % | Example 2 7 wt % | Example 3 14 wt % |
| | Unknown + coke | 27.28 | 0.11 | 0.06 | 0.83 |
| 350° C. | Total Ethanol Selectivity to | 100 100 | 100 100 | 100 100 | 100 100 |
| | Methane | 0.03 | 0.06 | 0.09 | 0.1 |
| | Ethylene | 5.5 | 15.4 | 17.8 | 27.8 |
| | Ethane | 0.4 | 1 | 1.6 | 0.82 |
| | Propylene | 8.8 | 12.5 | 13.9 | 14.6 |
| | Propane | 6.5 | 5.1 | 3.6 | 1.8 |
| | Butene | 8.9 | 14.1 | 15.2 | 15.5 |
| | Butane | 19.5 | 19.9 | 13.2 | 8.3 |
| | C5 + C6 | 6.3 | 15.2 | 19.2 | 18.9 |
| | Aromatics | 17.9 | 16.1 | 13.7 | 9.8 |
| | $CO_x$ | 0.02 | 0.08 | 0.1 | 0.2 |
| | C2=-C4= | 23.2 | 42 | 46.9 | 57.9 |
| | Unknown + coke | 26.15 | 0.56 | 1.61 | 2.18 |
| 400° C. | Total Ethanol Selectivity to | 100 100 | 100 100 | 100 100 | 100 100 |
| | Methane | 0.12 | 0.23 | 0.2 | 0.2 |
| | Ethylene | 6.2 | 9 | 14.6 | 18.9 |
| | Ethane | 0.7 | 1.1 | 1.5 | 1.1 |
| | Propylene | 10.1 | 13.3 | 19.4 | 20.1 |
| | Propane | 11.2 | 9.1 | 4.5 | 3.4 |
| | Butene | 6.6 | 9.5 | 12.2 | 14.1 |
| | Butane | 18.1 | 19.1 | 11.3 | 11.5 |
| | C5 + C6 | 2.4 | 7.2 | 9.9 | 12.1 |
| | Aromatics | 28.3 | 30.7 | 21.5 | 15.8 |
| | $CO_x$ | 0.1 | 0.5 | 0.6 | 1.1 |
| | C2=-C4= | 22.9 | 31.8 | 46.2 | 53.1 |
| | Unknown + coke | 16.18 | 0.27 | 4.3 | 1.7 |
| | Total | 100 | 100 | 100 | 100 |

What is claimed is:

1. A process to prepare propylene comprising contacting, at a temperature of from 300° C. to 500° C., ethanol and a rhenium oxide-modified ZSM-5 zeolite catalyst, wherein the rhenium oxide is present in or on the ZSM-5 zeolite in an amount from about 3 weight percent to about 15 weight percent, based on the weight of the catalyst as a whole, under conditions suitable to form propylene.

2. The process of claim 1, wherein conditions include a temperature from 300° C. to 400° C.

3. The process of claim 1, wherein the rhenium oxide-modified ZSM-5 zeolite catalyst is prepared by a process including impregnating, in an aqueous or organic medium, a ZSM-5 zeolite with a rhenium source, under conditions suitable to form a catalyst precursor, and calcining the catalyst precursor under conditions suitable to form the rhenium oxide-modified ZSM-5 zeolite catalyst.

4. The process of claim 3, wherein the organic medium is selected from the group consisting of alcohols, ethers, and combinations thereof.

5. The process of claim 3 or 4, wherein the rhenium source is selected from the group consisting of $Re_2O_7$, $ReO_3$, $Re_2O_5$, $ReO_2$, $Re_2O_3$, $ReF_7$, $ReCl_6$, $ReCl_5$, $ReCl_4$, $ReCl_3$, $ReS_2$, $NH_4ReO_4$, $NaReO_4$, $KReO_4$, and combinations thereof.

6. The process of claim 5, wherein the rhenium source is $NH_4ReO_4$.

7. The process of claim 3, wherein the rhenium oxide-modified ZSM-5 zeolite catalyst is in the form of a crystalline powder or an engineered extrudate comprising a binder.

8. The process of claim 1, wherein the amount of rhenium oxide ranges from 3 to 8 percent by weight, based on the rhenium oxide-modified ZSM-5 zeolite catalyst as a whole.

9. The process of claim 3, wherein the calcining is carried out at a temperature ranging from 450° C. to 550° C., for a time ranging from 3 to 5 hours.

* * * * *